(12) United States Patent
Motomura

(10) Patent No.: US 7,902,523 B2
(45) Date of Patent: Mar. 8, 2011

(54) FLUORESCENCE MICROSCOPE APPARATUS

(75) Inventor: Shinji Motomura, San Diego, CA (US)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 12/111,659

(22) Filed: Apr. 29, 2008

(65) Prior Publication Data

US 2008/0290293 A1 Nov. 27, 2008

Related U.S. Application Data

(60) Provisional application No. 60/927,237, filed on May 2, 2007.

(30) Foreign Application Priority Data

Mar. 18, 2008 (JP) ................................. 2008-069246

(51) Int. Cl.
*G01N 21/64* (2006.01)
(52) U.S. Cl. .................................................. 250/458.1
(58) Field of Classification Search ............... 250/458.1, 250/459.1, 461.1, 461.2; 359/385
See application file for complete search history.

(56) References Cited

U.S. PATENT DOCUMENTS

| 5,117,466 | A  | * | 5/1992 | Buican et al. | 382/133 |
| 6,690,463 | B2 | * | 2/2004 | Kask | 356/317 |
| 7,180,661 | B2 | * | 2/2007 | Sasaki | 359/385 |
| 7,330,255 | B2 | * | 2/2008 | Cluzel et al. | 356/318 |
| 7,336,355 | B2 | * | 2/2008 | Ishibashi et al. | 356/318 |
| 2004/0051051 | A1 | * | 3/2004 | Kato et al. | 250/458.1 |
| 2005/0024636 | A1 | * | 2/2005 | Nakamura | 356/318 |
| 2005/0122579 | A1 |   | 6/2005 | Sasaki | |
| 2006/0011861 | A1 |   | 1/2006 | Wolleschensky et al. | |
| 2007/0272842 | A1 | * | 11/2007 | Knebel et al. | 250/234 |
| 2008/0048105 | A1 |   | 2/2008 | Wolleschensky et al. | |

FOREIGN PATENT DOCUMENTS

EP 1617375 1/2006

OTHER PUBLICATIONS

Gratton et al., "Fluorescence lifetime microscopy: A stimulated-emission approach," 1996, Proceedings of SPIE, vol. 2678, pp. 98-109.*
Digman et al., "Fluctuation correlation spectroscopy with a laser-scanning microscopy: Exploiting the hidden time structure,", 2005, Biophysical Journal: Biophysical Letters, pp. L33-L36.*
So et al., "Two-photon single particle tracking in 3-D," 1997, Proceedings of SPIE, vol. 2983, pp. 45-56.*

(Continued)

*Primary Examiner* — David P Porta
*Assistant Examiner* — Kiho Kim
(74) *Attorney, Agent, or Firm* — Scully, Scott, Murphy & Presser, P.C.

(57) ABSTRACT

To observe and analyze intermolecular interactions such as diffusion and/or binding behaviors of molecules in a sample in a reacting state against optical stimulation, while applying the optical stimulation to a desired region in the sample by irradiating stimulus light. There is provided a fluorescence microscope apparatus comprising: a fluorescence image-capturing optical system; a stimulus light-irradiation optical system which includes a scanner for; a control unit which acquires temporal observation data by repeatedly capturing images using said image-capturing optical system while applying optical stimulation using the stimulus light-irradiation optical system; an analysis unit; and a display unit.

4 Claims, 8 Drawing Sheets

OTHER PUBLICATIONS

Herman et al., "Fluorescence lifetime imaging in cell biology," 1996, Proceedings of SPIE, vol. 2678, pp. 88-97.*

Wang et al., "Theoretical analysis of the radiation force applied in the particles in FCS,", 2005, Proceedings of SPIE, vol. 5630, pp. 911-917.*

Pilarczyk et al., "The combined use of UV-labile calcium chelators and calcium sensitive dyes in a microscope with two light sources influencing different regions in a group of coordinated contracting cardiac myocytes," 1997, Proccedings of SPIE, vol. 3197, pp. 177-186.*

Otomo et al., "Inter- and intra-molecular energy transfers of encapsulated dyes in dendrimers," 2002, Proceedings of SPIE, vol. 4798, pp. 37-43.*

Gullapalli et al., "Integrated multimodal microscopy, time-resolved fluorescence, and optical-trap rheometry: toward single molecule mechanobiology," Jan./Feb. 2007, Journal of Biomedical Optics, vol. 12, No. 2, pp. 014012-1-014012-17.*

Berland et al., "Two-photon fluorescence correlation spectroscopy: Method and application to the intracellurlar environment,", Feb. 1995, Biophysical Journal, vol. 68. pp. 694-701.*

Spring et al., "Application of a novel 8x8 PMT-array detector to light microscopy," 1998, SPIE Proceedings, vol. 3261, pp. 17-20.*

Spring et al., Application of a novel 8x8 PMT-array detector to light microscopy, 1998, SPIE Proceedings, vol. 3261, pp. 17-20.*

Digman, Michelle, A., et al., "Measuring Fast Dynamic in Solutions and Cells with a Laser Scanning Microscope", Biophysical Journal, vol. 89, Aug. 2005, pp. 1317-1327.

Wiseman, Paul W., et al., "Spatial mapping of integrin interactions and dynamics during cell migration by Image Correlation Microscopy", Journal of Cell Science 117, pp. 5521-5534.

Extended European Search Report dated Dec. 11, 2009.

* cited by examiner

US 7,902,523 B2

FLUORESCENCE MICROSCOPE APPARATUS

CROSS-REFERENCE TO RELATED APPLICATIONS

This application claims the benefit of U.S. Provisional Application No. 60/927,237, filed May 2, 2007.

BACKGROUND OF THE INVENTION

1. Field of the Invention

The present invention relates to a fluorescence microscope apparatus.

This application is based on Japanese Patent Application No. 2008-0692246, the content of which is incorporated herein by reference.

2. Description of Related Art

Raster Image Correlation Spectroscopy (RICS, refer to Document 1 below), Image Correlation Spectroscopy (ICS, refer to Document 2 below), and other methods have been studied and developed as algorithms for measuring and analyzing diffusion and binding behaviors, and moving directions of intracellular molecules in a living biological sample such as living cells, and such methods are attracting the attention of researchers.

Document 1: Michelle A. Digman, Measuring Fast Dynamics in Solutions and Cells with a Laser Scanning Microscope, Biophysical Journal Vol. 89, 2005.

Document 2: Paul W. Wiseman, Spatial mapping of integrin interactions and dynamics during cell migration by Image Correlation Microscopy, Journal of Cell Science 117, 2004.

Such analysis methods for determining diffusion coefficients and the like are carried out on the basis of image data of an analyte, which are obtained as scanned images through a laser scanning microscope. The image data to be used consist of scanned images of a sample in a static state.

BRIEF SUMMARY OF THE INVENTION

It is an object of the present invention to provide a microscope apparatus capable of observing and analyzing intermolecular interactions such as diffusion and/or binding behaviors of molecules in a sample in a reacting state against optical stimulation, while applying the optical stimulation to a desired region in the sample by irradiating stimulus light.

In order to achieve the above object, the present invention provides the following solutions.

The present invention provides a fluorescence microscope apparatus comprising: a fluorescence image-capturing optical system for capturing fluorescence images of a sample; a stimulus light-irradiation optical system which includes a scanner for applying optical stimulation to an optional region in the sample by irradiating stimulus light; a control unit which acquires temporal observation data by repeatedly capturing images using the image-capturing optical system while applying optical stimulation using the stimulus light-irradiation optical system, an analysis unit which analyzes intermolecular interactions through analysis of changes in fluorescence intensity caused by molecular fluctuations within a confocal volume with use of the temporal observation data; and a display unit which displays an analysis result from the analysis unit.

In the above invention, said irradiation optical system may include a scanning optical system which irradiates a point in the sample with excitation light while scanning the excitation light being irradiated at the point; and said fluorescence image-capturing optical system may have a confocal aperture for confocal detection of fluorescence light emitting from the sample.

Moreover, in the above invention, said irradiation optical system may include a scanning optical system which irradiates a point in the sample with excitation light that generates fluorescence through multiphoton absorption while scanning the excitation light being irradiated at the point.

The above invention may also be designed such that: said irradiation optical system irradiates a surface of the sample with excitation light; said fluorescence image-capturing optical system includes an imaging optical system which projects the fluorescence images on a two-dimensional imaging element; and said analysis unit carries out analysis using each pixel of the two-dimensional imaging element as a confocal volume.

Moreover, in the above invention, said analysis unit may execute Raster Image Correlation Spectroscopy (RICS).

Furthermore, in the above invention, said analysis unit may execute Image Correlation Spectroscopy (ICS).

The above invention may also comprise a region specifying unit which specifies a desired region with respect to the temporal observation data, wherein said analysis unit carries out analysis of diffusion and/or binding behaviors of molecules caused by the optical stimulation, with use of the fluorescence intensity data within the specified region.

According to the present invention, an effect capable of observing and analyzing intermolecular interactions such as diffusion and/or binding behaviors of molecules in a sample in a reacting state against optical stimulation, while applying the optical stimulation to a desired region in the sample by irradiating stimulus light, is demonstrated.

DETAILED DESCRIPTION OF THE INVENTION

First Embodiment

Figure 1:
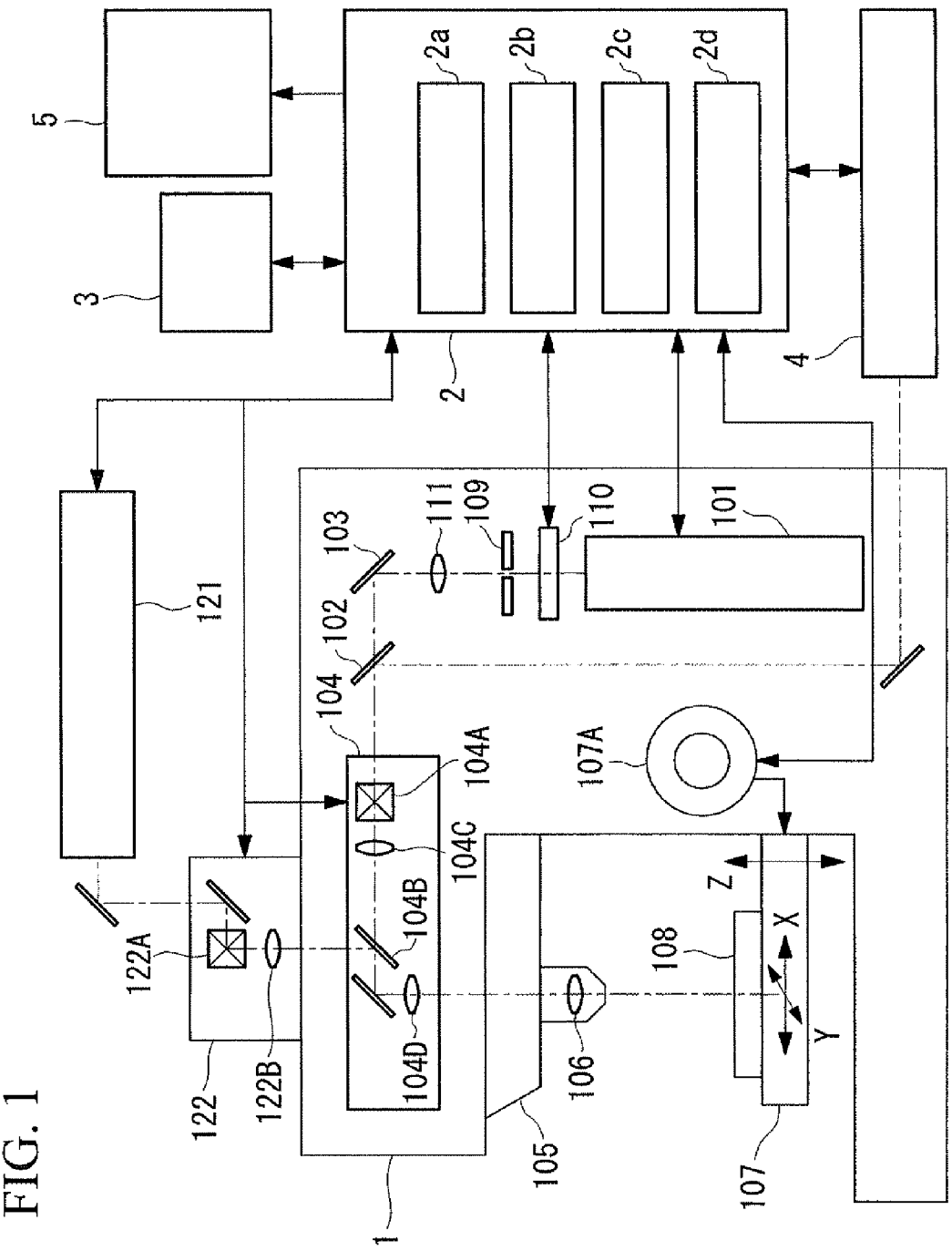
FIG. 1 is an entire schematic diagram showing a fluorescence microscope apparatus according to a first embodiment of the present invention.
Figure 2:
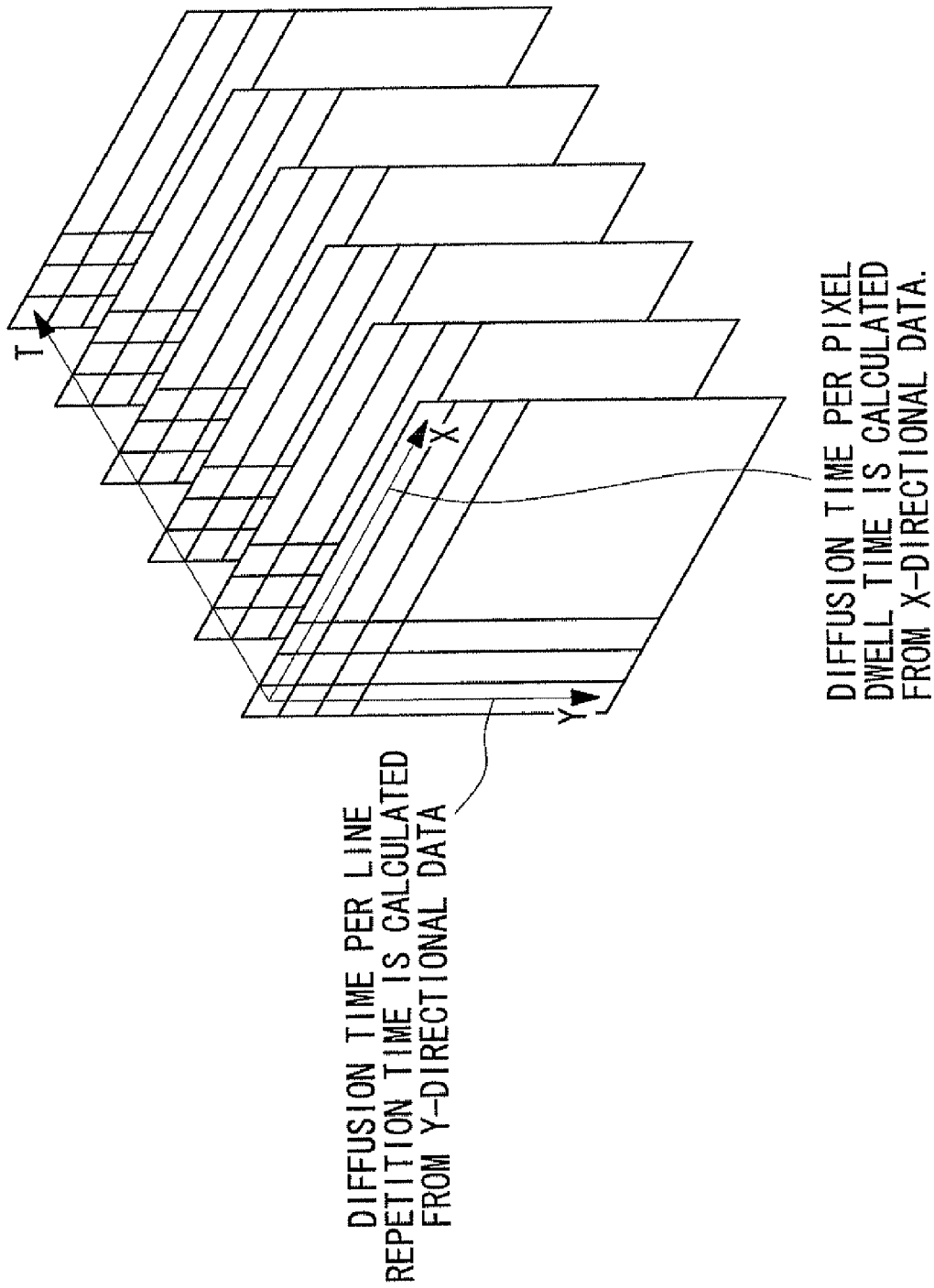
FIG. 2 is an explanatory diagram showing temporal observation images (XY-T images) captured by the fluorescence microscope apparatus of FIG. 1.

FIG. 1 shows a schematic configuration of a scanning microscope apparatus (fluorescence microscope apparatus) according to a first embodiment of the present invention.

In FIG. 1, the reference symbol 1 denotes a scanning microscope main body. The scanning microscope main body 1 is connected with a computer (control unit) 2. The computer 2 is also connected with an operation panel (region specifying unit) 3, an excitation laser device 4, a stimulation laser device (stimulus light-irradiation optical system) 121, and an image monitor (display unit) 5.

In the scanning microscope main body 1, an excitation (observation) laser beam emitting from the excitation laser device 4 is reflected by an excitation dichroic mirror (fluorescence image-capturing optical system) 102 and made incident into a scanning unit (scanning optical system) 104. The scanning unit 104 comprises a scanner 104A and a composing mirror 104B. In the drawing, the reference symbol 104C denotes a pupil projection lens, and the reference symbol 104D denotes a focusing lens.

The scanner 104A has a galvanometer mirror for scanning in the X axis direction and a galvanometer mirror for scanning in the Y axis direction. The scanner 104A scans a laser beam from the excitation laser device 4 in the X and Y axis directions according to a scan control signal from the computer 2. Moreover, the composing mirror 104B is a dichroic mirror for composing the excitation (observation) laser beam and a stimulation laser beam that will be described later. The composing mirror 104B allows transmission of excitation (observation) laser beams (such as fluorescence from a sample) and other observation light (such as visible light and IR) but reflects stimulation laser beams (such as UV and purple light).

The excitation (observation) laser beam, which has been scanned in the X and Y axis directions, passes through the composing mirror 104B, and is irradiated as a spotlight on an observation sample (sample) 108 placed on a stage 107, via an object lens 106 attached to a revolver 105.

Light from the observation sample 108 caused by the irradiation on the spotlight, such as reflected light, or fluorescence light emitting from the observation sample 108, is collected by the object lens 106 to return to the incident optical path. The collected light passes through the dichroic mirror 102, and light having wavelengths to be detected is exclusively extracted through a barrier filter (fluorescence image-capturing optical system) 110.

The detection light that has passed through the barrier filter 110 is let incident into a photoelectric converter (fluorescence image-capturing optical system) 101 such as a photomultiplier, and is subjected to photoelectric conversion into electric signals corresponding to the quantity of the detection light. The analog signals output from the photoelectric converter are converted into digital signals corresponding to the quantity of detection light, by an A/D input channel 2b installed in the computer 2. A calculating/processing unit (analysis unit) 2a in the computer 2 combines these digital signals and the scanning position information of the scanner 104A to construct a two dimensional image. The image thus constructed is saved in a memory 2c and output as visual information on the image monitor 5.

In the present scanning microscope apparatus, arrangement of a confocal aperture (fluorescence image-capturing optical system) 109 in a conjugate position with respect to the observation sample 108 enables use as a confocal scanning microscope apparatus that exclusively detects light from the focus position to make an image while eliminating light from sources other than the focus position. The reference symbol 103 denotes a mirror (fluorescence image-capturing optical system), and the reference symbol 111 denotes a confocal lens (fluorescence image-capturing optical system).

Moreover, in the present scanning microscope apparatus, use of infrared pulse laser which generates two-photon excitation for the excitation laser device 4 and detection of fluorescence generated by the two photon excitation enable use as a multiphoton excitation scanning microscope apparatus that exclusively observes the position of collected excitation laser beams in a three dimensional space of a sample, even without the confocal aperture 9.

The stage 107 is an electrically-operated stage which is movable in the X and Y directions which are orthogonal to the optical axis of the microscope (object lens 106). Moreover, the revolver 105, or the stage 107 with use of a Z motor 107A provided inside or outside the microscope, enables focus position control in the Z direction. The Z direction is the direction of the optical axis of the microscope (object lens 106). The position control in the X, Y, and Z directions is controlled by the computer 2.

On the other hand, the scanning unit 104 is connected with a stimulus light irradiation unit 122. The stimulus light irradiation unit 122 also has a galvanometer mirror for scanning in the X axis direction and a galvanometer mirror for scanning in the Y axis direction as a scanner 122A, to scan a stimulation laser beam from the stimulation laser device 121 in the X and Y axis directions according to a scan control signal from the computer 2. The reference symbol 122B denotes a pupil projection lens.

It is also possible to irradiate stimulus light at one desired point on the sample by holding the X and Y galvanometer mirrors which constitute the scanner 122A at desired angles. The laser beam, which has been scanned in the X and Y axis directions, is reflected by the composing mirror 104B in the scanning unit and is composed with the excitation (observation) laser beam. The composite beam travels through the object lens 106 attached to the revolver 105, and is irradiated as a spotlight on the observation sample 108 placed on the stage 107.

The operation panel 3 has a pointing device such as a track ball, a joystick, or a mouse, as well as a keyboard. The operation panel 3 accepts instructions input by an observer, and outputs an instruction to start scanning a laser beam and a command to capture an image as well as outputs to the computer 2 a command to adjust the sensitivity of the photoelectric converter 101. Moreover, the operation panel is also used to set the wavelengths and intensities of an excitation (observation) laser beam and a stimulation laser beam, and to specify a region of interest (ROI) when an excitation (observation) laser beam or a stimulation laser beam is to be irradiated exclusively on a desired point or region (ROI) within a field of view of one screen.

The computer 2 takes charge of control of the entire apparatus. In particular, when an instruction to scan is input from the operation panel 3, the computer 2 outputs a scan control signal to the scanning unit 104 and the stimulus light irradiation unit 122. Also, the computer 2 converts analog signals of the observation sample 108 from the photoelectric converter 101 into digital data through the A/D input channel, transfers the digital data to the memory 2c, and displays the image and the scanning menu on the image monitor 5.

Furthermore, the computer 2 is designed to make settings such as the sensitivity of the photoelectric converter 101 (e.g., applied voltage in cases of a photomultiplier), the amplifier gain, and the offset, in accordance with a sensitivity adjustment command from the operation panel 3. Moreover, programs 2d in the computer 2 execute respective controls such as control of the scanning unit in the scanning microscope main body 1, injection of a laser beam from the excitation laser device 4 into the microscope, and output of the image information from the memory to the image monitor 5.

As a technique for analyzing molecular dynamics such as diffusion and binding behaviors, and moving directions, there is a technique called Raster Image Correlation Spectroscopy (RICS). The RICS technique is a technique in which: a scanning microscope capture temporal observation images (XY-T images) are captured under scanning conditions where one pixel size is sufficiently small as compared to the spot size of an excitation laser beam (for example, 60×/NA 1.42 magnification of the object lens and 5× zoom of the scanner (galvanoscanner)); and the autocorrelation function (Equation (1), refer to academic Document 1 for details) is employed to determine a diffusion coefficient of molecules per pixel dwell time and per line repetition time, based on time intervals of the pixel scanning time and the line scanning time for capturing the image data. The temporal observation images (XY-T images) refer to a group of a series of XY images captured in one certain observation position repeatedly for a plurality of times at predetermined time intervals.

$$G_S(\xi, \psi) = S(\xi, \psi) \times G(\xi, \psi) \quad (1)$$

$$S(\xi, \psi) = \exp\left(-\frac{\frac{1}{2}\left[\left(\frac{2\xi\delta r}{W_O}\right)^2\right]}{\left(1 + \frac{4D(\tau_p\xi + \tau_1\psi)}{W_O^2}\right)}\right)$$

$$G(\xi, \psi) = \frac{\gamma}{N}\left(1 + \frac{4D(\tau_p\xi + \tau_1\psi)}{W_O^2}\right)^{-1}$$

Figure 3:
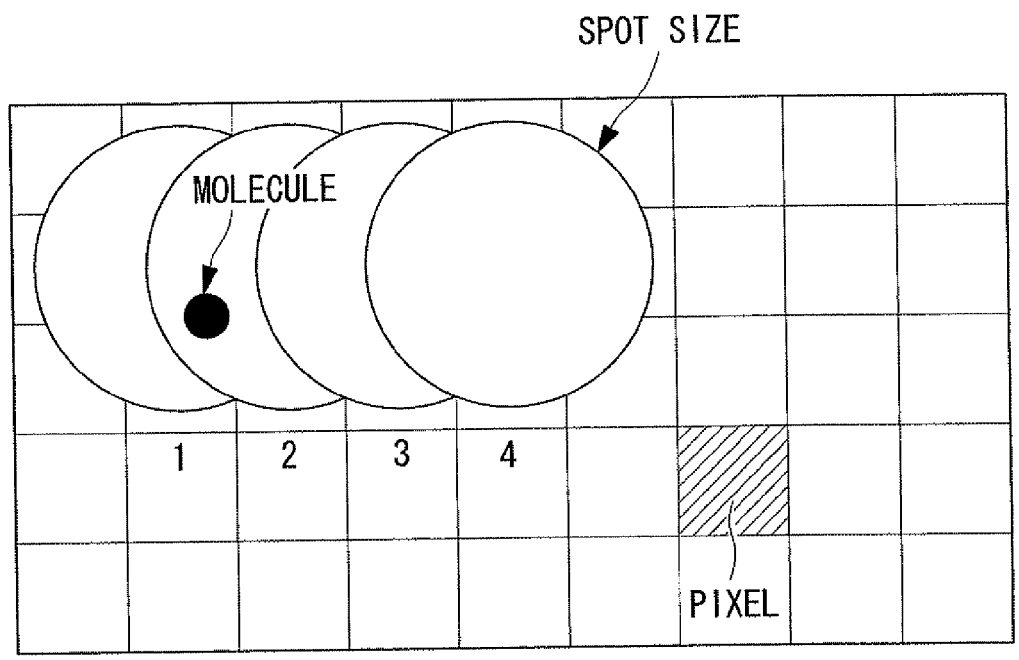
FIG. 3 is a diagram illustrating a relation between a molecule in a static state and laser beam spots.

When a particle stays still or is slowly moving, a fluorescence signal emitting from the molecule is detected by several spots as shown in FIG. 3. In the case of FIG. 3, the fluorescence signal from the molecule is detected only by the first spot and the second spot. Application of the RICS technique to the temporal observation data obtained through observation of such a molecule provides a small diffusion coefficient.

Figure 4:
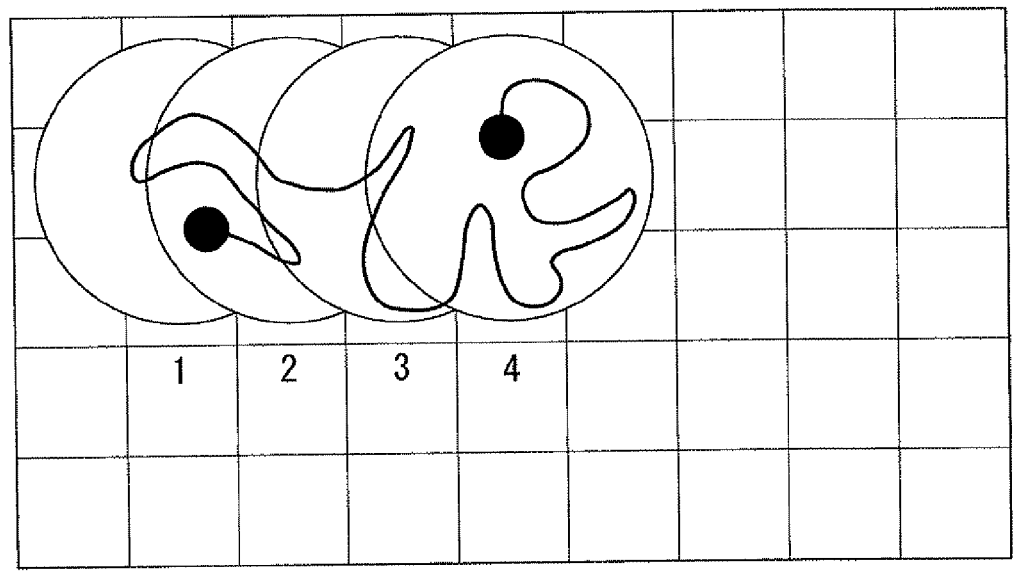
FIG. 4 is a diagram illustrating a relation between a molecule in a moving state due to diffusion and laser beam spots.

When a particle is rapidly moving, a fluorescence signal emitting from the molecule is detected by many spots as shown in FIG. 4. In the case of FIG. 4, the fluorescence signal from the molecule is detected by all of the first spot to the fourth spot. Application of the RICS technique to the temporal observation data obtained through observation of such a molecule provides a large diffusion coefficient. The magnitude correlation between these diffusion coefficients enables analysis of the difference in the diffusion rate of respective molecules.

Figure 5:
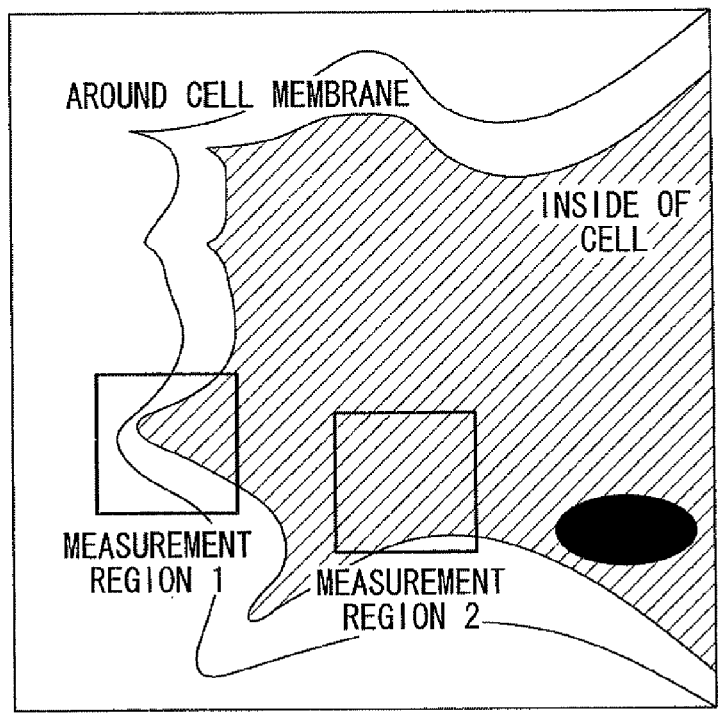
FIG. 5 is a diagram showing a measurement region within a temporal observation image captured by the fluorescence microscope apparatus of FIG. 1.

The measurement of the diffusion rate can be achieved not only by calculation processing of the entire field of view of the temporal observation image, but also by specifying a desired measurement region in the temporal observation image as shown in FIG. 5 and targeting fluorescence signals in the measurement region. By using this processing, diffusion of intracellular molecules and binding behaviors of molecules around the cell membrane can be captured as one temporal observation image, and can be observed and measured at a same time point.

Next, the operation of the first embodiment using the system configured as mentioned above is described.

Figure 6:
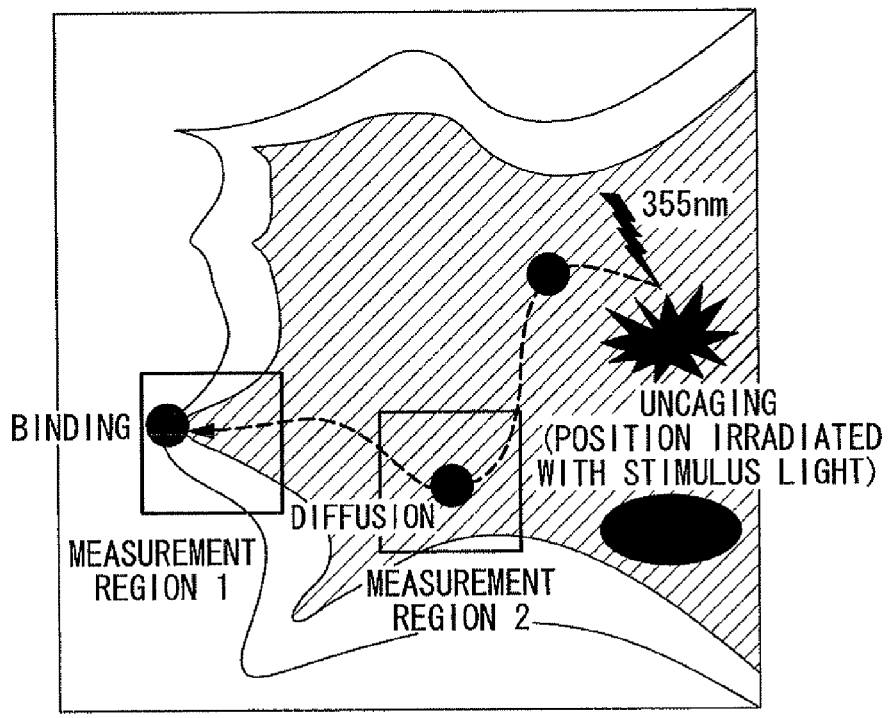
FIG. 6 is a diagram illustrating a movement of a molecule due to diffusion when a stimulation laser beam for uncaging is irradiated at a position away from the measurement region of FIG. 5.
Figure 7:
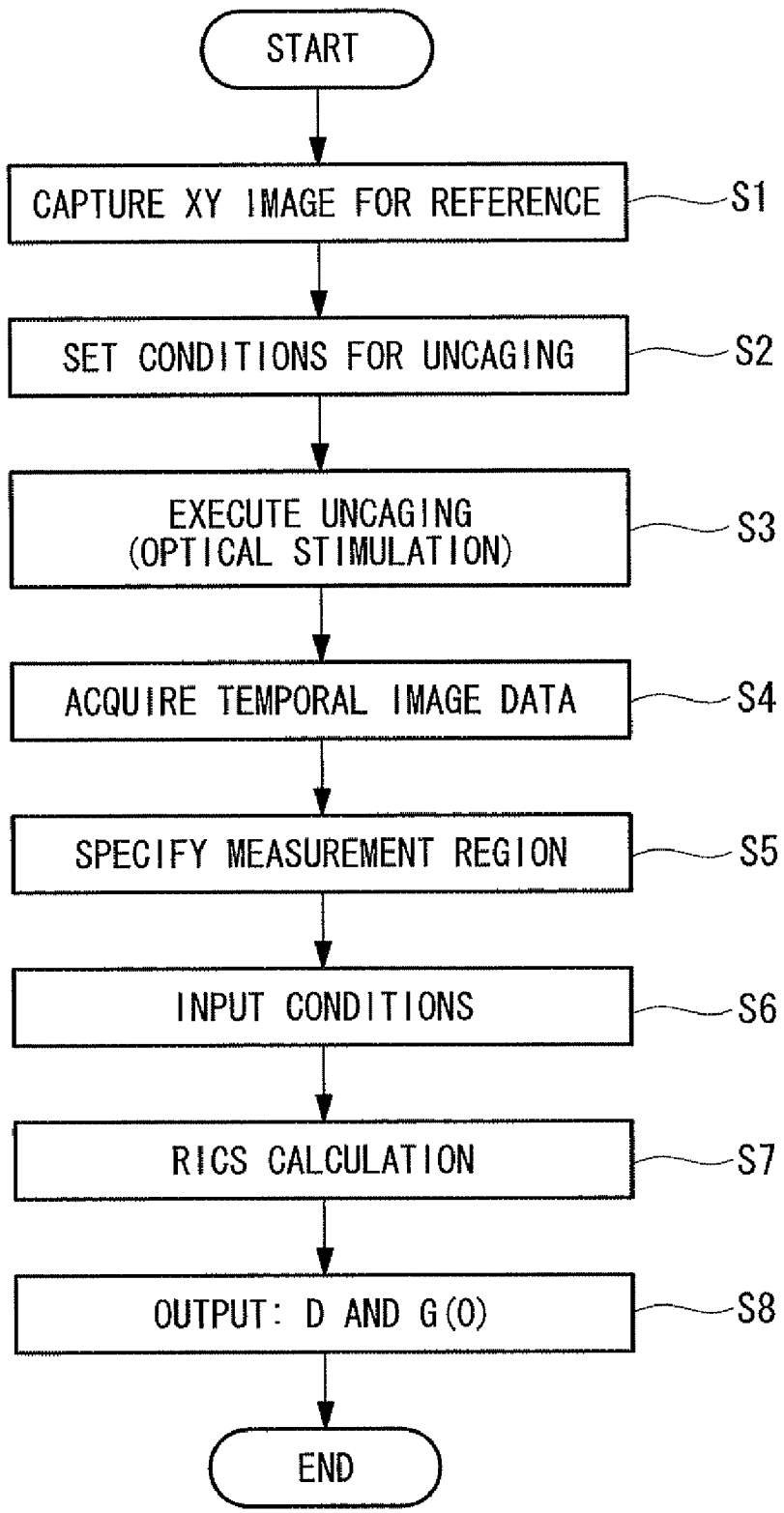
FIG. 7 is a flowchart illustrating a procedure for specifying and analyzing the measurement region of FIG. 5.

As an example, here is a description of a case where a sample injected with a caged indicator and a fluorescence indicator, which is sensitive to calcium ion concentration, is irradiated with an excitation laser beam having a wavelength of 488 nm from the excitation laser device 4 (FIG. 1), to carry out analysis by detecting fluorescence generated from the calcium ion concentration-sensitive fluorescence indicator. FIG. 6 shows the manner in which the sample reacts against optical stimulation for uncaging when applied to a desired position of the sample. FIG. 7 shows the procedure (flowchart) for specifying and analyzing the measurement region of the sample in this manner.

Step S1) First, in order to specify the position to be uncaged (=optically stimulated), an observation image (reference image (XY image)) of the site to be measured is captured and displayed as a reference image on the image monitor 5.

Step S2) Using the reference image, the position or region (ROI, FIG. 6) to be optically stimulated (uncaged) is specified.

Steps S3 and S4) Condition settings for temporal observation (XY-T image capturing) of the sample are specified or input. Examples of the condition settings include the number of X pixels, the number of Y pixels, information on the object lens (magnification and numerical aperture), the zoom size of scanning (information on the scanning width for laser scanning), the laser wavelength, the scan rate (pixel rate, line rate, and frame interval), and the number of frames to be captured.

Scanning of an excitation laser beam is started to capture XY-T images; while, as shown in FIG. 6, irradiating the specified position or region with a stimulation laser beam having a wavelength of 355 nm from the stimulation laser device 121 (FIG. 1) to apply stimulation such that the caged group of the caged reagent is cleaved. The manner in which the calcium ion concentration is changed by the substance released from the caged reagent at this time is saved in the memory 2c of the computer (FIG. 1) as temporal observation data, and is displayed on the image monitor 5 (FIG. 1) as T (time) series images.

Step S5) In the temporal observation data displayed on the image monitor 5, a measurement region is formed around the cell membrane using the operation panel 3 (FIG. 1).

Steps S6 to S8) Fluorescence signals within the measurement region are processed with the RICS technique. Conditions required for the RICS calculation have been already set as the XY-T image capturing conditions in Steps S3 and S4). The pixel size can be calculated from the XY-T image capturing conditions (number of X pixels, number of Y pixels, magnification of the object lens, and zoom size of scanning). D (diffusion coefficient) and G(0) are calculated based on these parameters and the Equation (1).

Here, "G(0)=1/N (N is the number of molecules)" means the value of the autocorrelation function $G(\tau)=(\Delta F(t)\Delta F(t+\tau))/F(t)^2$ in the case where $\tau=0$ (initial value). The concentration of molecules is discussed in terms of this value.

By so doing, diffusion and binding behaviors of molecules around the cell membrane involved in the cleavage of the caged group can be measured.

In the present invention, a scanning microscope apparatus comprises a mechanism which controls optical stimulation independently of temporal observation by arranging another scanning optical system that is different from the optical system for capturing images, and an analysis method such as the RICS technique is applied to the temporal observation data acquired by capturing images with use of the scanning microscope apparatus, by which behaviors of intracellular molecules can be continuously analyzed during and after cell stimulation.

Second Embodiment

Figure 9:
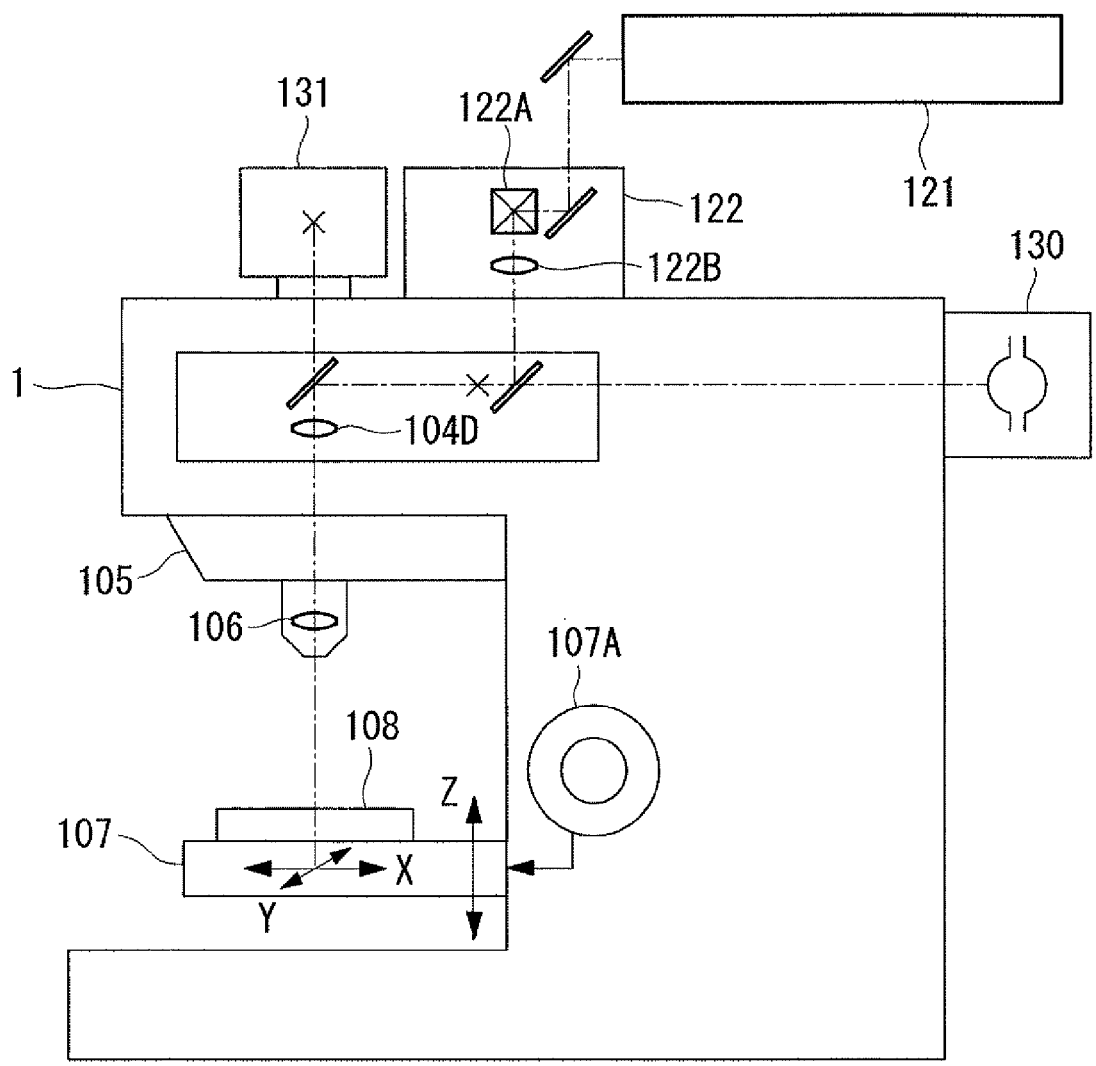
FIG. 9 is an entire schematic diagram showing a fluorescence microscope apparatus according to a second embodiment of the present invention.

As shown in FIG. 9, a fluorescence microscope apparatus uses a mercury lamp house 130 and a CCD camera (imaging optical system) 131, instead of the scanning unit 104 (FIG. 1), the excitation laser device 4 (FIG. 1), and the photoelectric converter 101 in the scanning microscope apparatus according to the first embodiment mentioned above. In such a fluorescence microscope apparatus, optical stimulation is applied with use of the stimulus light irradiation unit 122 (FIG. 1) according to the first embodiment during temporal observation to acquire the temporal observation data.

Figure 8:
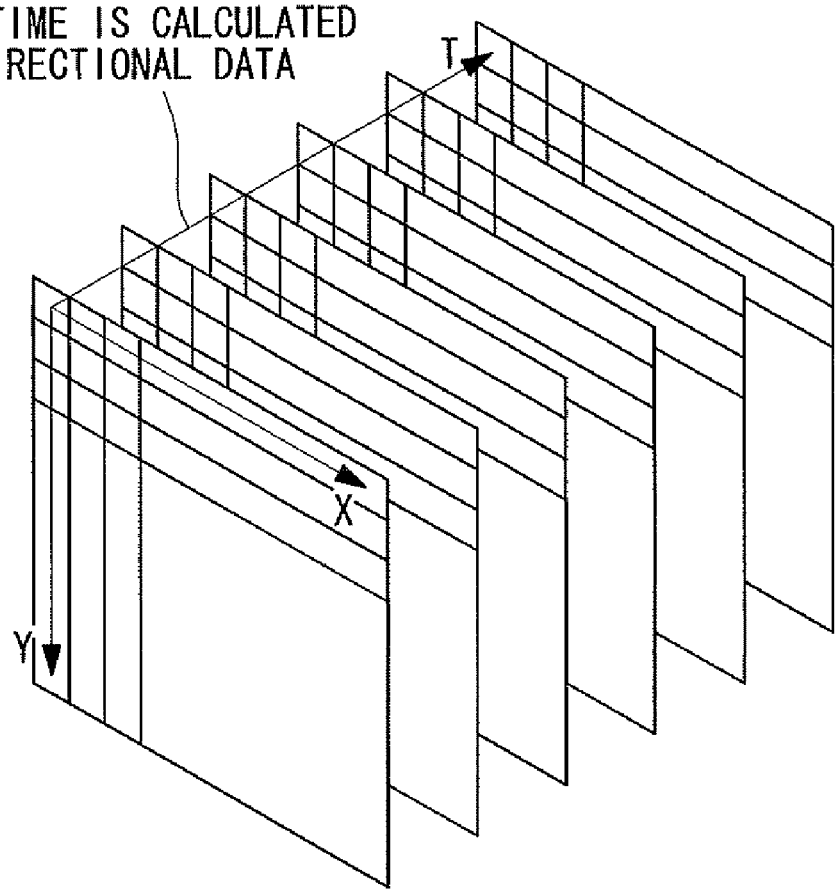
FIG. 8 is an explanatory diagram showing temporal observation images (XY-T images) captured by the fluorescence microscope apparatus of FIG. 1.

As shown in FIG. 8, the Image Correlation Spectroscopy (ICS) technique, which is capable of obtaining the diffusion coefficient per frame repetition time of the temporal observation data, is applied. By so doing, similarly to the first embodiment, behaviors of intracellular molecules can be continuously analyzed during and after cell stimulation.

The ICS technique is a technique for calculating the diffusion coefficient using information on brightness changes in the T direction for respective pixels in temporal image data. Since the resolution time for the information on the brightness changes is the time for capturing one frame, ICS is inferior to RICS in terms of speed. However, it is possible to calculate the diffusion coefficient even in the configuration of the present embodiment which employs non-confocal detection, by using the calculation technique of substituting one pixel in the CCD camera with a confocal volume.

ICS can also be used in the first embodiment.

Modified Example 1

Figure 10:
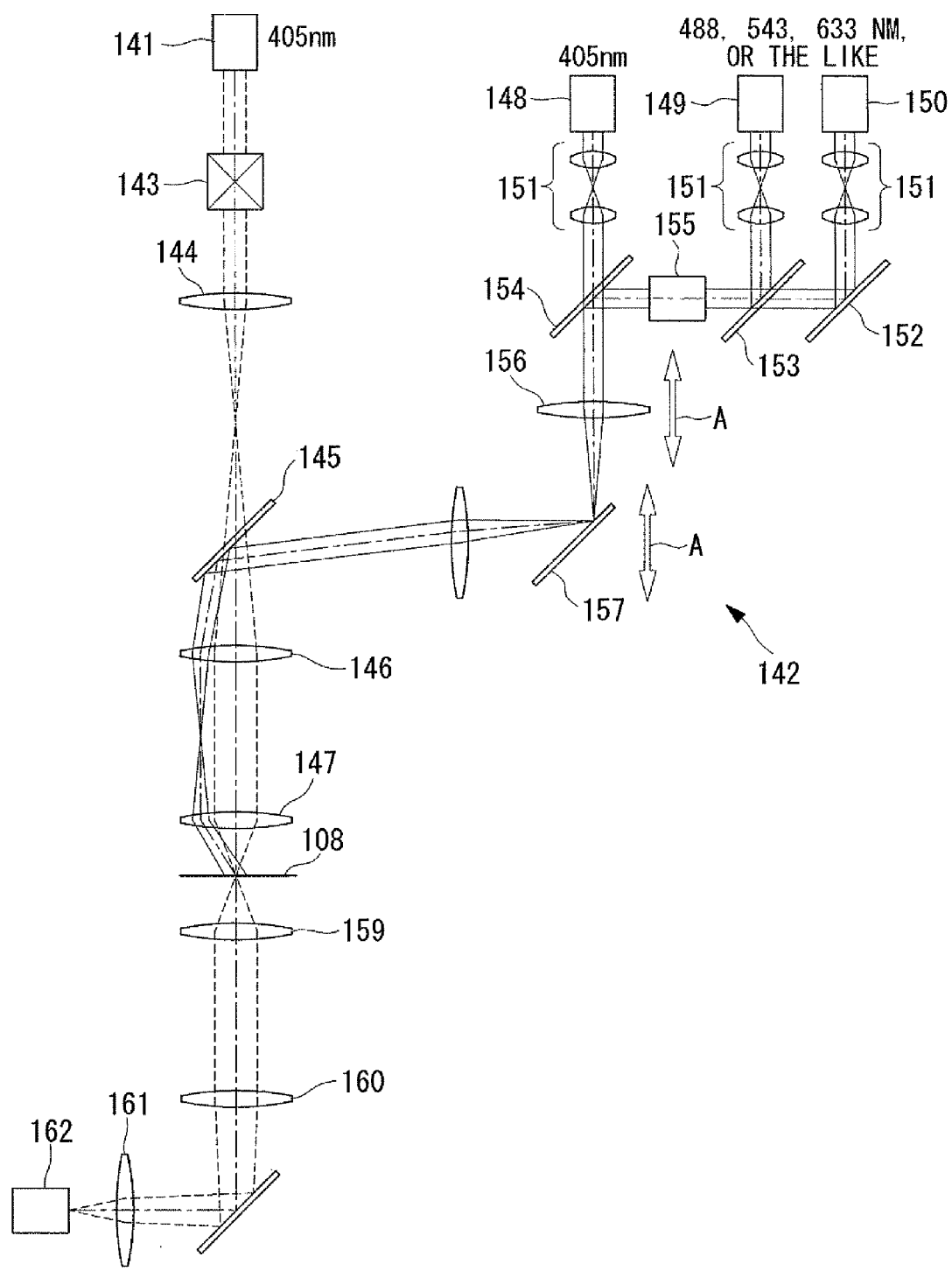
FIG. 10 is a diagram showing a modified example of the fluorescence microscope apparatus of FIG. 9.

A total internal reflection fluorescence microscope apparatus as shown in FIG. 10, which comprises a laser light source 141 and a total reflection illumination device 142, instead of the mercury lamp house in the fluorescence microscope apparatus according to the second embodiment mentioned above, can also be used.

The two dimensional position of a stimulation laser beam from the laser light source 141 is set by an XY galvano scanner 143. Then, the stimulation laser beam is irradiated on a sample S through a pupil projection lens 144, a dichroic mirror (or a half mirror) 145, a focusing lens 146, and an object lens 147, to apply optical stimulation to the observation sample 108.

The total reflection illumination device 142 comprises: laser light sources 148, 149, and 150 which emit laser beams of a plurality of wavelengths; beam expanders 151 which adjust the luminous flux diameter of laser beams from the respective laser light sources 148 to 150; a mirror 152; dichroic mirrors 153 and 154; an acoustooptic device 155 such as AOTF which modulates laser beams from the laser light sources 149 and 150; a variable magnification lens 156 for adjusting the illumination region, which is movable along the optical axis direction A; a drive mirror 157 for adjusting the blurring amount, which is moved along the optical axis direction A to thereby adjust the deflection angle so as to adjust the incident angle of laser beams into the specimen; and a pupil projection lens 158.

Moreover, the total internal reflection fluorescence microscope apparatus comprises: an object lens 159 arranged on the opposite side to the object lens 147 relative to the observation sample 108; a focusing lens 160; a variable magnification lens 161; and an electron multiplier CCD 162.

With the dichroic mirror 145, laser beams from the laser light sources 148 to 150 are converged along the optical path of the stimulation laser beam from the laser light source 141 and made incident at shallow angles that satisfy total reflection conditions with respect to the observation sample 108.

With use of the total internal reflection fluorescence microscope apparatus, behaviors of intracellular molecules in the observation sample 108 such as cells can be continuously analyzed during and after cell stimulation, by using temporal observation data having a high signal/noise ratio, within the depth resolution of about 100 nm from the surface of a cover glass.

According to the present invention, a microscope apparatus comprises a mechanism which controls optical stimulation independently of temporal observation by arranging another scanning optical system that is different from the scanning optical system or fluorescence observation optical system for capturing images, and an analysis method such as the RICS technique is applied to the temporal observation data acquired by capturing images with use of the microscope apparatus, by which behaviors of intracellular molecules can be continuously and accurately analyzed during and after cell stimulation.

What is claimed is:

1. A fluorescence microscope apparatus comprising:
   an irradiation optical system which generates fluorescence by irradiating an image capture region of a sample with excitation light as a spotlight;
   a fluorescence image-capturing optical system for capturing fluorescence images of image capture region;
   a stimulus light-irradiation optical system which includes a scanner for applying only optical stimulation to an optional region in the sample by irradiating stimulus light, the optional region differing from the image capture region in size and/or shape;
   a control unit which acquires temporal observation data by repeatedly capturing images using the image-capturing optical system while applying optical stimulation using the stimulus light-irradiation optical system;
   an analysis unit which analyzes two-dimensional distribution of diffusion and/or binding behaviors of molecules through analysis of changes in fluorescence intensity caused by molecular fluctuations within a confocal volume of the sample by executing raster image correlation spectroscopy with use of the temporal observation data of the image capture region; and
   a display unit which displays an analysis result from the analysis unit, wherein
   said irradiation optical system includes an excitation scanner that two-dimensionally scans the irradiated excitation light on the image capture region of the sample, and
   said fluorescence image-capturing optical system has a confocal aperture for a confocal detection of fluorescence light under the conditions where one pixel size is smaller than the spotlight size of the excitation light, the fluorescence light emitted from a position where the excitation light is irradiated.

2. A fluorescence microscope apparatus according to claim 1, wherein said irradiation optical system generates fluorescence through multiphoton absorption.

3. A fluorescence microscope apparatus according to claim 1, comprising:
   a region specifying unit which specifies a part of the image capture region in which the temporal observation data is acquired as a desired region with respect to the temporal observation data, wherein
   said analysis unit carries out analysis of diffusion and/or binding behaviors of molecules caused by the optical stimulation, with use of the fluorescence intensity data within the specified region.

4. A fluorescence microscope apparatus according to claim 1, wherein the pixel size is half the size or less than a diameter of the spotlight size of the excitation light.

* * * * *